United States Patent
Lin (12)

(10) Patent No.: US 6,392,091 B2
(45) Date of Patent: *May 21, 2002

(54) PROCESS OF PURIFYING AND PRODUCING HIGH PURITY AROMATIC POLYCARBOXYLIC ACIDS

(76) Inventor: Tsong-Dar Vincent Lin, 5672 Sugar Hill Dr., Houston, TX (US) 77056

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/286,262

(22) Filed: Apr. 5, 1999

Related U.S. Application Data

(60) Provisional application No. 60/109,648, filed on Nov. 24, 1998.

(51) Int. Cl.⁷ .............................................. C07C 51/42
(52) U.S. Cl. ...................................... 562/485; 562/486
(58) Field of Search ................................. 562/485, 486

(56) References Cited

U.S. PATENT DOCUMENTS 5,565,609 A * 10/1996 Hirowatari et al. ......... 562/485
5,767,311 A    6/1998 Lee et al. ................... 562/487
5,840,968 A * 11/1998 Lee et al. ................... 562/486

FOREIGN PATENT DOCUMENTS

EP          0551596 A2       7/1993
WO         WO 98/12157   *  3/1998

* cited by examiner

*Primary Examiner*—Paul J. Killos
*Assistant Examiner*—Taylor V. Oh
(74) *Attorney, Agent, or Firm*—Moser, Patterson & Sheridan, LLP

(57) ABSTRACT

The present invention provides a solvent extraction purification method for aromatic polycarboxylic acids that meet or exceed polymer-grade specification. The method includes dissolving a crude aromatic polycarboxylic acid in a base compound; removing impurities and excessive base compound; and removing residual base compound while making purified product. The purification method removes not only the impurities from the crude acid, but also the residual base compound from finished product that otherwise will contaminate the product. The salt in the cake is converted to product by acid-substitution, thermal decomposition, or electrolysis. The method uses base-extraction solvents to extract base compound and impurities from the salt. The residual base compound in the recovered product is then removed by leaching, stripping, thermal agitating with electromagnetic waves, or evaporation with thermal decomposition. The purification method allows eliminating crystallizers for crystallization and equipment for drying and pneumatically carrying. Finally, the purification method is combined with the oxidation and solvent recovery in prior art to use only one set of process steps, instead of two, to produce aromatic polycarboxylic acids.

38 Claims, No Drawings ic acid (2,6-NDA), 2,7-
PROCESS OF PURIFYING AND PRODUCING HIGH PURITY AROMATIC POLYCARBOXYLIC ACIDS This application claims the benefit of provisional application 60/109,648 filed Nov. 24, 1998.

FIELD OF THE INVENTION

This invention relates to aromatic polycarboxylic acids, especially to an improved process of purifying and producing aromatic polycarboxylic acids in high purity.

BACKGROUND OF THE INVENTION

Aromatic polycarboxylic acids have been produced through the oxidation of the corresponding alkyl group with molecular oxygen. Examples of such acids are pure terephthalic acid (PTA), isophthalic acid (IPA), trimellitic acid (TMA), 2,6-naphthalene dicarboxylic acid (2,6-NDA), 2,7-naphthalene dicarboxylic acid (2,7-NDA), and others. Since PTA is the most typical process, it will be used for illustrations in the invention. However, the purification and production methods of the instant invention are applicable for all aromatic polycarboxylic acids.

A predominant process for making PTA consists of the following steps to prepare crude terephthalic acid (CTA).
1) Oxidization: The reaction of p-xylene (PX) with air is carried out in a liquid phase at 150–230° C. and 150–425 psia using cobalt-manganese-bromine as catalysts and acetic acid as solvent.
2) Crystallization: The effluent from the reactor is crystallized through 3 to 5 large crystallizers at a reduced pressure and temperature to precipitate terephthalic acid from mother liquor.
3) Filtration: The crude acid is then separated from mother liquor by centrifugation/filtration. The mother liquor, with or without treatment, is recycled to the oxidation step.
4) Drying: The crude acid is dried by blowing inert gas, and the acetic acid carried by inert gas is then recovered by a scrubber. The dried crude terephthalic acid is pneumatically carried to a silo or storage bin that requires large nitrogen flow or an air separation plant for some PTA plants.
5) Solvents and catalysts recovery: Solvent and catalysts are recovered by various processes.

CTA containing about 0.5% impurities is then purified by a hydrogenation process to produce polymer-grade PTA containing about 25 PPM of 4-carboxybenzaldehyde (4-CBA), 150 PPM of p-toluic acid, and about 0–50 PPM of benzoic acid. Similar to CTA, the purified PTA from hydrogenation unit goes through another set of process steps: crystallization; filtration; and drying as described above. Thus, to remove impurities from reactor effluent at about 0.5% to a purified product at about 0.025%, the predominate process uses the following expensive steps:
1) Requiring two sets of process steps for crystallization, centrifugation/filtration, drying, and pneumatically carrying equipment.
2) Using expensive purification process by chemical reaction. Disregarding the higher capital cost of hydrogenation unit, high production cost is required because of operating under high temperature and pressure by using expensive noble metals as catalyst.
3) Requiring long resident time for crystallization. CTA takes about 3–5, and PTA takes about 5, large crystallizers to recover product from mother liquor. In addition, due to highly corrosive bromine-acetic acid environment, some crystallizers may require using expensive corrosive-resistant material, such as titanium-lined equipment.
4) Requiring drying and pneumatically carrying to make finished product.
5) Meeting polymer-grade specification, but product still containing about 0.01% of impurities.

PTA in high purity is required to be suitable for making polyester fibers, films, and molding resin. Terephthalic acid is difficult to be purified due to its low solubility in most solvents, high boiling temperature, and similarities in physical and chemical properties with impurities present.

An alternative is to remove impurities by solvent extraction. The solvent extraction approach is attractive because of lower costs. It can be the traced back to 1953 (U.S. Pat. No. 2,664,440), or even earlier. In early stage, solvents suggested are unstable, reactive with the product, toxic, or unable to purify CTA to desired level. Thereafter, Iwane (U.S. Pat. No. 5,344,969) and Hirowatari (U.S. Pat. No. 5,565,609) disclosed methods that use more stable solvents. The following summarizes these methods.
1) Dissolving crude acid: The aromatic polycarboxylic acid forms salt with many base compounds, and the salt is soluble in a dissolving solvent such as water or alcohol at elevated temperature.
2) Removing impurities: Some impurities can be easily separated by solution pretreatment, such as activated carbon for colorants. The impurities having close properties with the acid are separated in mother liquor by crystallizing with cooling for at least 30° C.
3) Recovering product: Hirowatari thermally decomposes the solution from pretreatment by heating or contacting steam with a concentrated solution in the presence of alkylene glycol. Iwane precipitates and washes the salt that is then converted to a purified product by thermally decomposing or by adding an acid-substitution solvent to substitute the product acid in the salt. Iwane also recovers product by directly adding an acid-substitution solvent to the solution.

Both Iwane and Hirowatari use amine compound consisting of nitrogen as the only hetero atom, such as aliphatic, alicyclic, aromatic, or heterocyclic amines. Iwane uses an alcohol as the dissolving solvent for the purification of crude NDA from oxidation. Hirowatari uses water as the dissolving solvent to recover aromatic dicarboxylic acids from hydrolyzed polyester resins. In his approach, no purified salt is prepared because its impurities consist of only additives and colorants that can be simply removed by activated carbon. Thus, this method is suitable for purifying hydrolyzed resins containing already highly purified PTA with colorants or additives that are easy to be separated, but not for the crude aromatic dicarboxylic acids from oxidation containing impurities that are difficult to be separated.

For thermal decomposition, Iwane adds heat to the salt that may be dispersed in a paraffin, alkylbenzene, alkylnaphthalene, or alkylbiphenyl, and does not use steam for heating. The chosen solvents have high boiling temperature that will be presented in the finished product as another contaminant. Hirowatari heats the pretreated aqueous solution while refluxing to decompose the amine salt, or concentrates the solution by distillation before contacting with steam to decompose and remove the amine compound. Alkylene glycol is used to raise reflux temperature. The refluxing increases the content of base compound in the finished product, and the distillation has to evaporate more than 50% of water that requires significant energy.

Iwane claims improving 2,6-NDA purity from 97.2% to about 99.8%, and Hirowatari recovers a hydrolyzed resin to a 99.9% PTA. Iwane applies his method to crude NDA from reactor effluent at a purity level lower than CTA that is purified to a level only close to CTA. Although both approaches improves product purity, they are still off from the specification of polymer-grade PTA (>99.98%).

The other approach is Lee (U.S. Pat. No. 5,767,311) that uses N-methyl pyrrolidone (NMP) to dissolve CTA between 140–190° C. without using a dissolving solvent. The solution is cooled to 5–50° C. for crystallization. Filtering and washing the precipitate make a PTA meeting polymer-grade specification without using means to recover product from salt. However, experiments using this method indicate that unconverted salts contaminate the finished product. The contamination may be from the failure to recognize the existence of salt formed by NMP and PTA in the process. Lee identifies the precipitation from solution as PTA, but it is actually a salt. The salt is converted to product during washing by some of his washing solvents, such as methanol. However, significant salts are unconverted because only washing is insufficient to convert all salts to product. The dissolution process and solvent recovery of the method are expensive. Compared with amine compound or morpholine, NMP is about 2–3 times more expensive and requires 3–5 times more to dissolve the crude acid. It also costs more to heat and recover the high boiling solvent. In addition, Lee incorrectly asserts that CTA can be dissolved in a nonaqueous morpholine solution. Its solubility is negligible disregarding solution temperature unless water is presented. Even if morpholine were able to dissolve CTA, the finished product is not a PTA but a salt, because methanol cannot convert morpholine salt to PTA. The difference in NMP and morpholine salts will be further discussed and taken advantaged by the present invention. The present invention uses new crystallization process and washing solvent to improve product quality of this method.

Disregarding the advantages there is no known commercial application of purification by solvent extraction. A major problem is from the fact that the residual base compound remaining in the finished product becomes a contaminant itself All proposed organic base compounds contain nitrogen that causes color and other problems in making polyesters, and no prior art discusses the problem and teaches how to remove the base compound from the finished product.

Crystals always contain residual solvent by inclusion during crystallization. Using the known methods, it may contain more than 0.1% of residual base compound that is close to the impurity level of CTA. To be suitable for making polyesters, the residual base compound has to be removed to a few parts per million that is close to the impurity level of PTA. Therefore, the previously known prior art of solvent extraction removes impurities in the crude acid, but introduces residual base compound as contaminant in the product that makes it unsuitable for making polyesters.

The known methods do not attempt to remove residual base compound from the finished product. Iwane teaches using acid solvent, Hirowatari teaches using water to wash base compound from the filter finished product cake, and Lee teaches using NMP, p-xylene, acetone, methyl ethyl ketone, or methanol to wash the filter cake. An experiment using 100:1 ratio of water to wash and leach the cake for about 10 hours, produces a purified product still contains significant amount of base compound. This indicates that the base compound is difficult to be removed once it is included in product crystalline. This problem is either unknown for having not been addressed in open literatures, or known by those highly skilled in the art, but remained to be unsolved.

The prior art of solvent extraction purification methods either specifically or implicitly suggest replacing hydrogenation unit and uses CTA as feed except Lee. Lee incorrectly asserts that high percentage of CTA can be directly recovered from filtering reactor effluent without using crystallization or other means. Because most CTA remain in the mother liquor of reactor effluent, and it requires long residence time to precipitate CTA. Therefore, the predominated process uses 3–5 large crystallizers to recover CTA. The instant invention suggests using flashing and evaporation to reduce residence time.

Because the purification method itself needs another set of process steps for crystallization, filtration, drying, and pneumatically carrying, the prior art also requires two sets of process steps to produce PTA. Thus, using the known methods of solvent extraction for producing aromatic polycarboxylic acids suffers the following disadvantages:

1) Introducing base compound that contaminates the finished product.
2) Requiring two sets of process steps for crystallization, centrifugation/filtration, drying, and pneumatically carrying equipment.
3) Significant detectable impurities remaining in the purified product.
4) Requiring long resident time for crystallization, and thus, several large crystallizers.
5) Requiring drying and pneumatically carrying to make finished product.

Accordingly, several objects of the present invention are:

1) To provide a solvent extraction purification method to remove impurities from the crude acid to meet or exceed the specification of polymer-grade aromatic polycarboxylic acids.
2) To remove the base compound from purified product so that it will be suitable for making polyester fibers, films, molding resin, or other applications.
3) To provide a process for producing polymer-grade aromatic polycarboxylic acids that requires only one set of process steps to substantially reduce capital and production costs.
4) To reduce the number of crystallizers required for crystallization, or eliminate them.
5) To produce aromatic polycarboxylic acids that may be used directly for making polyesters without requiring drying and pneumatically carrying steps.

Further objects and advantages will become apparent from the disclosed solvent extraction method that unexpectedly and surprisingly removes impurities to undetectable level by the current standard HPLC measurement.

SUMMARY OF THE INVENTION

The present invention provides a solvent extraction purification method for aromatic polycarboxylic acids that meet or exceed polymer-grade specification. The method includes dissolving a crude aromatic polycarboxylic acid in a base compound; removing impurities and excessive base compound; and removing residual base compound while making purified product. The purification method removes not only the impurities from the crude acid, but also the residual base compound from finished product that otherwise will contaminate the product. The salt in the cake is converted to product by acid-substitution, thermal decomposition, or electrolysis. The method uses base-extraction solvents to extract base compound and impurities from the salt. The residual base compound in the recovered product is then removed by leaching, stripping, thermal agitating with electromagnetic waves, or evaporation with thermal decomposition. The purification method allows eliminating crystallizers for crystallization and equipment for drying and pneumatically carrying. Finally, the purification method is combined with the oxidation and solvent recovery in prior art to use only one set of process steps, instead of two, to produce aromatic polycarboxylic acids, and capital and production costs are substantially reduced.

DETAILED DESCRIPTION OF THE INVENTION

The present invention provides a solvent extraction purification method for aromatic polycarboxylic acids that meet or exceed polymer-grade specification. The method applies to any polycarboxylic acid such as PTA, IPA, TMA, 2,6-NDA, 2,7-NDA, and others. It includes dissolving a crude aromatic polycarboxylic acid in a base compound; removing impurities and excessive base compound; and removing residual base compound while making purified product. The preferred base compound contains both oxygen and nitrogen as hetero atom, such as morpholine or NMP. Additional base compounds are discussed in more detail below. The salt in the cake is then converted to product by acid-substitution solvent, thermal decomposition, or electrolysis.

In addition to removing impurities from crude acids, the method uses base-extraction solvents to extract base compound and impurities from the salt and recovered product. The residual base compound in the recovered product is removed by leaching, stripping, thermal agitating with electromagnetic waves, or evaporation with thermal decomposition. The residual base compound is not an impurity but a contaminant introduced by the purification process. The method allows eliminating crystallizers for crystallization and equipment for drying and pneumatically carrying to reduce costs. Finally, the purification method is combined with the oxidation and solvent recovery in prior art to use only one set of process steps, instead of two, to produce aromatic polycarboxylic acids.

The crystal of aromatic polycarboxylic acid purified by solvent extraction typically contains base compound and other solvents through the mechanism of adsorption on crystal surfaces; entrapment in cracks, crevices, and agglomerates; and inclusion of pockets of liquid. The base compound in the crystal does not present as liquid but as solid salt formed with the product crystalline or acid-substitution solvent. Washing or thermal decomposition may remove some of the adsorbed or the entrapped but not the included solid that is shielded by the product crystalline with subliming temperature around 300–425° C. This makes the removal of residual base compound from product crystalline extremely difficult.

Prior art prevents oxidizing the base compound by conducting under an inert atmosphere to avoid deteriorating the product color that hides the existence of base compound. The standard HPLC analysis technique used to measure impurities cannot detect non-aromatic base compounds; color measurement of purified product cannot detect the base compound either, unless the compound is intentionally oxidized to show its existence. A simple technique to detect the presence of residual base compound is to burn the finished product in air to non-white color at high temperature for a long period of time. The degree of the presence of residual base compound can then be detected by comparing the degree of whiteness with the PTA purified by hydrogenation, or using existing technique of color measurement.

In a purified salt, the base compound not bonded to the carboxylic acid functional group is excessive base compound. Removing the excessive base compound in the salt cannot avoid the recovered product contacting base compound because the compound is also a constituent of salt. Thus, additional process is required to remove the residual base compound included inside the recovered product crystalline, and it is difficult and unobvious.

The instant invention finds base-extraction solvents that extract both base compounds and impurities from the purified salt and recovered product. A suitable base-extraction solvent is any non-nitrogen-containing compound having low solubility for a targeted crystalline or having capability to convert salt to product acid; high solubility for the base compound and impurities; and easy to be separated, or not required to be separated, from the finished product. The solvent may contain hydroxyl, carbonyl, ether, ketone, ester, or other functional group.

Unless it is specifically specified, the solvent extraction method is conducted in a range of temperature from the freezing temperature to the highest boiling temperature of the solution at a predetermined pressure, and preferably from the chilled water temperature to the highest boiling temperature. The operation pressure is not particularly limited; it may vary from 0 to 100, and preferably from 0.001 to 5, atmosphere absolute.

The purification method for removing impurities and residual base compounds comprises the following process steps.

Dissolving Crude Acid

A crude aromatic polycarboxylic acid is dissolved in a base compound by forming a salt. If the salt can be dissolved in a dissolving solvent, then it will be used to enhance solubility and reduce dissolution cost. Otherwise, no dissolving solvent is used. This also includes the rare case that a crude acid is dissolved in a base compound without forming a salt.

The crude aromatic polycarboxylic acid can be from any source containing any kind of impurity. It can be from oxidation reactor, intermediate production streams, such as in the production of dimethyl terephthalate (DMT) or dimethyl-2,6-naphthalene dicarboxylate (NDC), hydrolyzed polyester, or others. The base compound includes oxygen containing base compound and non-oxygen containing base compound. The oxygen containing base compound includes any compound having oxygen and nitrogen as hetero atoms, such as morpholine compounds, amide compounds, inorganic bases, and others. The non-oxygen containing base compound comprises amine compound and ammonia. The base compound includes aliphatic, alicyclic, aromatic, and heterocyclic compounds. The amount of base compound used is 0.5–100 mole per mole of carboxylic functional group in the aromatic polycarboxylic acid, preferably 1–2 mole per mole of carboxylic functional group in the crude aromatic polycarboxylic acid. The dissolving solvent comprises water, alcohol, ether, ketone, and ester. The amount of dissolving solvent may vary from 0–100, preferably 1–10, mole per mole of carboxylic functional group in the crude aromatic polycarboxylic acid.

The prior art uses conventional heating to dissolve the crude acid by transferring energy from solvent molecules to the salt ions to overcome the attraction force. In addition of using the conventional heating, the invention may dissolve the crude acid by thermal agitation under electromagnetic waves. Thermally agitating an ionized solution under electromagnetic waves differs from the conventional or microwaves heating. The wave provides thermal agitation to both solvent molecules and salt ions. However, the ions receive far more energy so that the ions heat up the molecules instead of the reverse way of the other heating. Thus, it has distinct characteristics, such as solubility, solvent evaporation, and crystallization. For instance, it has different solubility because the salt ions receive more energy to dissolve but may also be thermally decomposed back to acid; better crystallization efficiency because higher vapor evaporation and less solvent for crystallization; and different precipitation mechanism because high energy ions may be used to thermally decompose a portion of salts to product acid. The main advantage is its significant saving in dissolution energy and time. Less dissolution time reduces solvent degradation or reaction with impurities.

Iwane and Hirowatari use non-oxygen containing amine compound, and Lee uses pyrrolidone compound, an alicyclic amide compound having characteristics of carbonyl and amine functional groups. The other preferred oxygen containing base compound is morpholine compound having characteristics of ether and amine functional groups. The oxygen containing organic base compound has significant different characteristics from the non-oxygen containing base compound in basicity, dielectric constant, dipole moment, or hygroscopic with the dissolving solvent. The present invention takes the advantage of the characteristics to remove base compound and impurities from the purified product.

The oxygen containing salt is called basic salts, and the non-oxygen containing salt is called normal salts. Most normal salts are soluble in many solvents such as water and alcohol. The salt containing ether group that will be called ether basic salt is soluble in water, but many are insoluble in other solvents, such as alcohol. The salt containing carbonyl group, will be called carbonyl basic salt, is insoluble in most solvents including water and alcohol. The solvent having low solubility for salt or capable to convert salt back to acid, but still having high solubility for impurities and base compound, is used as a base-extraction solvent to purify the salt or product. The present invention discovers that carbonyl basic salts are weakly bonded. Therefore, it is easier to recover the salt to product and remove its base compound from the product, but it is more difficult and expensive to form the salt. The reverse is true for ether basic salts. Thus, the base compound removes the impurities from the crude acid, and the base-extraction solvent removes base compound and impurities from the purified salt and finished product.

More specifically, the aromatic polycarboxylic acids are those having one or more condensed rings, wherein two or more carboxylic acid groups may be at any positions of the aromatic ring or rings, and any hydrogen may be substituted by any other functional groups. Examples of one-ring aromatic dicarboxylic acids include, but are not necessarily limited to terephthalic acid, isophthalic acid, orthophthalic acid, trimellitic acid, hemimellitic acid, trimesic acid, pyromellitic acid, and mellitic acid. Examples of two-ring aromatic polycarboxylic acids include, but are not necessarily limited to 2,6-naphthalene dicarboxylic acid, 2,7-naphthalene dicarboxylic acid, 1,7-naphthalene dicarboxylic acid, 1,8-naphthalene dicarboxylic acid, 2,3,6-naphthalene tricarboxylic acid, 1,4,5,8-naphthalene tetracarboxylic acid, and 2,3,6,7-naphthalene tetracarboxylic acid. Examples of three-condensing ring aromatic polycarboxylic acids include, but are not necessarily limited to 2,6-anthracene dicarboxylic acid, 2,7-anthracene dicarboxylic acid, 2,8-anthracene dicarboxylic acid, 2,9-anthracene dicarboxylic acid, 1,9-anthracene dicarboxylic acid, 2,3,6-anthracene tricarboxylic acid, 1,4,5,8-anthracene tetracarboxylic acid, and 2,3,6,7-anthracene tetracarboxylic acid. The aromatic polycarboxylic acid also includes a mixture of aromatic polycarboxylic acids, for instance, 2,6-naphthalene dicarboxylic acid and 2,7-naphthalene dicarboxylic acid, in any proportion.

For base compound, the nitrogen atom in a base compound may have three or five valences. The base compound includes all combinations of hetero-atom and carbon-atom at different positions of the compound, and their saturated and unsaturated compounds with one or more hydrogen atoms that may be substituted by an alkyl, aryl, or acyl group, or the ammonium salts derived from such compounds. If a base compound is in solid or gaseous state under normal condition, then its aqueous solution may be used. A base compound can be a mixture in any proportion. Inorganic bases may be sodium hydroxide, potassium hydroxide, etc.

The morpholine compounds comprise morpholine, N-methylmorpholine, N-ethylmorpholine, N-propylmorpholine, N-isopropylmorpholine, N-methylmorpholine oxide, N-phenylmorpholine, 4-morpholinepropionitrile, 1-morpholine-1-cyclohexene, or others. The other base compound containing ether group includes mono-heterocyclic compound containing 3 to 8 atoms having nitrogen and oxygen in the ring, and it comprises oxazocines, oxazepines, oxazines, oxazoles, isoxazoles, oxadiazetes, oxazirines, etc.

The amide compounds include aliphatic amide, such as dimethylformamide, dimethylacetamide, ethanamide, acetamide, and others. An alicyclic amide includes pyrrolidone, N-methyl-pyrrolidone, N-ethyl-pyrrolidone, N-alkyl-2-pyrrolidone, N-mercaptoalkyl-2-pyrrolidone, N-mercaptoethyl-2-pyrrolidone, N-alkyl-2-thiopyrrolidone, N-methyl-2-thiopyrrolidone, N-hydroxyalkyl-2-pyrrolidone, and N-hydroxyethyl-2-pyrrolidone, lactam, etc. An aromatic amide includes phenylacetamide, phenylene terephthalamide, etc.

The aliphatic amine comprises methylamine, dimethylamine, trimethylamine, ethylamine, diethylamine, triethylamine, n-propyamine, di-n-propylamine, tri-n-propylamine, isopropylamine, diisopropylamine, triisopropylamine, ethylenediamine, N-methylethyleneamine, N,N-dimethylethylenediamine, N,N'-dimethylethylenediamine, N,N,N'-trimethylethylenediamine, N,N,N',N'-tetramethylethylenediamine, 1,2-diaminopropane, 1,3-diaminopropane, monoethanolarnine, diethanolamine, triethanolamine, dimethylacetamide, dimethylformamide, etc. The alicyclic amine comprises methylcyclohexylamine, N-methylcyclohexylamine, N,N-dimethylcyclohexylamine, ethylcyclohexylamine, N-ethylcyclohexylamine, N,N-diethylcyclohexylamine, isopropylcyclohexylamine, N-isopropylcyclohexylamine, N,N-diisopropylcyclohexylamine, ethylene imine, propylene imine, etc. The aromatic amine comprises N,N-dimethylaniline, N,N-diethylaniline, N,N-dibutylaniline, N,N-dimethyltoluidine, N,N-diethyltoluidine, etc. The heterocyclic amines includes pyridine, piperidine, N-methylpiperidine, N-methylpyrrolidine, etc.

The preferred base compound is morpholine, N-methylpyrrolidone, trimethylamine, triethyalamine, or triethanolamine.

The alcohol includes aliphatic monohydric alcohol such as methanol, ethanol, n-propanol, isopropanol, n-butyl alcohol, isobutyl alcohol, sec-butyl alcohol, tert-butyl alcohol, n-amyl alcohol, isoamyl alcohol, sec-amyl alcohol, tert-amly alcohol, neopentyl alcohol, hexyl alcohol, heptyl alcohol, octyl alcohol, nonyl alcohol, and decyl alcohol; alicyclic monohydric alcohol such as cyclopentyl alcohol and cyclohexyl alcohol; aliphatic straight-chain diols such as ethylene glycol, diethylene glycol, propylene glycol, butanediol, and pentanediol; alicyclic diols such as 1,2-cyclopentanediol, 1,3-cyclopentanediol, 1,2-cyclohexanediol, 1,3-cyclohexanediol, 1,4-cyclohexanediol; and aliphatic polyols such as glycerol and pentaerythritol. Aliphatic monohydric alcohol having 3 or less carbon atoms and diols having 4 or less carbon atoms, are preferred. An alcohol can be a mixture of these in any proportion. The preferred alcohol is methanol, ethanol, or alkylene glycol.

Ether includes dimethyl ether, diamyl ether, diethyl ether, isopropyl ether, n-butyl ether, n-hexyl ether, chlorodimethyl ether, phenyl methyl ether, dibenzyl ether, ethylene oxide, dioxane, trioxane, furan, tetrahydrofuran, methyl-tetrahydrofuran, tetrahydropyran, methyl-tetrahydropyran, and others. Ketone includes acetone, methyl ethyl ketone, methyl n-propyl ketone, methyl n-butyl ketone, methyl amyl ketone, methyl acetone, 2-methyl cyclopentanone, cyclopentanone, cyclohexanone, cyclohexanol, and others. Ester includes ethylene glycol methyl ether, diethylene glycol methyl ether, ethylene glycol ethyl ether, diethylene glycol ethyl ether, ethylene glycol butyl ether, ethylene glycol ethyl ether, ethylene glycol benzyl ether, diethylene glycol, triethylene glycol, alkyl formate, alkyl acetate, alkyl propionate, oxalates, alkyl lactate, carbonates, benzoates, and others.

Removing Impurities and Excessive Base Compound

This step removes impurities by pretreating, precipitating, separating, and washing the cake. Impurities may be removed by solution pretreatment and crystallization by cooling as taught in the prior art. In addition, the instant invention provides new processes to remove both the impurities and excessive base compound from the washed cake.

Solution pretreatment is to remove the impurities that can be easily separated from solution, such as colorants or additives by activated carbon, insolubles by filtration, or floats by overflowing or scraping. Processes that separate this kind of impurities are already well known, and the invention is not restricted to any specific one. If the crude does not contain this kind of impurity, solution pretreatment is not required.

Crystallization is to remove the impurities that are difficult to be separated and have close physical and chemical properties with the product. The solubility of impurity salt is either lower or higher than the product salt at a given temperature and solution composition. By the variation of solution temperature and/or composition, the impurity having lower solubility is precipitated first and separated from the others. Precipitating the product salt separates it from those having higher solubility by leaving them in mother liquor.

Prior art uses crystallization by cooling to separate impurities, and the salt is separated by usual process, such as filtration or centrifugation. It requires several large crystallizers for crystallization because long residence time is needed for growing crystals from mother liquor. The alternative is crystallization by controlling composition with cooling to reduce residence time requirement. After completely dissolving the crude acid and before crystallization, it removes a predetermined amount of solvent by usual processes, such as evaporation or distillation, so that the cooled slurry still contains sufficient mother liquor to separate the impurities. It reduces but still requires significant residence time for crystallization. Both try to keep as much impurities in mother liquor as possible for the separation from the purified salt.

The prior art usually uses base compound to wash filter salt because the dissolving solvent dissolves the salt immediately. However, the washing efficient is low due to the high viscosity of salt. Besides, it saturates the salt with excessive base compound and increases the content of base compound in the finished product. Other prior art teaches using aliphatic hydrocarbons or aromatic hydrocarbons as washing solvent. It simply replaces the solvent in crystal and provides no extraction power, and may present in the finished product as other contaminant.

The instant invention uses base-extraction solvent to remove both excessive base compound and impurities from the salt. The new process includes washing and leaching with base-extraction solvent, crystallizing salt in the presence of a base-extraction solvent, precipitating product in the presence of a base-extraction solvent, crystallization with direct-extraction from salt, and crystallization with resalting and salt base-substitution.

Most base-extraction solvents do not convert salt to acid. However, some may if the pure solvent is used to wash the filter carbonyl basic salt, but mixing the salt-converting base-extraction solvent with the base compound in a proper proportion reduces the salt conversion. For instance, mixing methanol with 50% NMP to wash the filter salt significantly reduces salt conversion. The washed cake is preferred to be retained as salt.

More specifically, the base-extraction solvent is water, hydrogen peroxide, alcohol, ether, phenol, ketone, ester, and others. The alcohol, ether, ketone, and ester are defined previously. The base-extraction solvent may be used alone or as a mixture of two or more in any proportion, and the solvent may be used in liquid or vapor state. The preferred base-extraction solvent is water, methanol, ethanol, alkylene glycol, acetone, tetrahydrofuran or tetrahydropyran. Since the targeted crystalline in this step is purified salt, the used dissolving solvent is excluded. In the next step, the targeted crystalline is product acid and it may include the used dissolving solvent.

The color of most impurity salts are non-white and the odor of excessive base compound is ammoniacal, using base-extraction solvent to wash or leach the filter cake improves the salt significantly in both of the color and odor compared with the salt washed by other solvents, such as base compound or hydrocarbons. By definition, leaching is different from washing filter cake (Perry's Chemical Engineering Handbook, $6^{th}$ Edition, Page 19–48). Processes for washing and leaching are very well known, and the invention is not limited to any specific one.

The base-extraction solvent may also be added to the solution after complete dissolution of the crude acid. The presence of base-extraction solvent during crystallization reduces the inclusion of base compound and simultaneously extracts impurities and base compound from the salt. In addition, the presence of base-extraction solvent in the solution changes crystallization mechanism, such as shape, size, and rate. For instance, adding methanol, acetone, or tetrahydrofuran, changes the shape and increases the size of crystals from NMP-PTA salts.

The purified product can be precipitate in the presence of a base-extraction solvent by adding an acid-substitution solvent to the solution. The presence of a base-extraction solvent extracts impurities and base compound from the precipitate. The present invention discovers that water is a base-extraction and also an acid-substitution solvent for carbonyl basic salts because it precipitates product directly from a saturated solution, but other base-extraction solvents, such as methanol, precipitate salt in a range of solution composition. However, the solubility of 4-CBA and NMP salt in water is about 10 times lower than methanol. Compared with washing to convert salts in the prior art, precipitating product in the presence of a base-extraction solvent has better control of salt conversion and crystal size by adjusting temperature, agitation, composition, and residence time. An acid-substitution solvent is added to precipitate product without the presence of a base-extraction solvent in the prior art. However, the product purity is low because most impurities precipitate with the product.

Removing most or all solvents out of the solution by evaporation or flashing obtains solid or slurry of salt. Since impurities are not vaporized under normal operating conditions, they all remain with the salt. This is a situation to be avoided by the crystallization of prior art that keeps impurities in mother liquor for separation. However, the invention unexpectedly and surprisingly finds that the base-extraction solvent can extract most of impurities and excessive base compounds from the salt. Thus, this crystallization process completely eliminates the residence time requirement for crystallization. Its product recovery efficiency depends on the solubility of the salt in the base-extraction solvent and the amount of dissolving solvent remained in the slurry. Unlike the crystallization of prior art, the crystallization with direct-extraction from salt does not cool the solution for crystallization. The mother liquor in slurry may or may not be separated from the salt before adding base-extraction solvent. The extracted solution is then separated from the salt by usual separation processes.

Redissolving the precipitate in the dissolving solvent or base compound and recrystallizing the solution for one or more times will remove impurities to undetectable level by the current standard HPLC method or to meet polymer grade specification for a crude acid having higher impurities. Thus, crystallization with resalting comprises the steps of crystallizing the salt from the dissolved solution of the crude acid; separating, washing, and redissolving the salt; recrystallizing the salt from the solution; and separating and washing the salt by usual process. Preferably, the salt is completely dissolved before recrystallization. If the washed cake contains product acid from using electromagnetic waves or washing with a salt-converting base-extraction solvent, the acid may or may not be separated from the salt or redissolved by the base compound for resalting. Any previously discussed crystallization process can be used for crystallization and reprecipitation. However, it is preferable to use the crystallization with direct-extraction from salt for both of crystallization and recrystallization. If precipitating product in the presence of a base-extraction solvent is used, it is preferred to be the last crystallization step. The number of resalting is not specifically limited, and preferably 1–2 times.

The base-extraction solvent used in the previously discussed processes for removing impurity may or may not be the same. The amount used is 0.1–100, preferably 1–10, moles per mole of the carboxylic functional group. For ether basic salts, the preferred base-extraction solvent is methanol or ethanol. For carbonyl basic salts, alkylene glycol, acetone, tetrahydrofuran, or tetrahydropyran is also preferred.

Salt base-substitution is a method that enhances product recovery by substituting the base compound of a first salt with the base compound of another salt. As discussed previously, carbonyl basic salts are more difficult and expensive to prepare but easier and cheaper to recover. For instance, preparing an NMP-PTA salt is several times more expensive than a morpholine-PTA salt, but it can be recovered by less expensive water. The instant invention discovers that the base compound of a salt can be substituted by another base compound having higher boiling temperature, and therefore, an ether basic salt or a common salt can be converted to a carbonyl basic salt. Thus, a salt can be prepared by a more economic base compound and converted to another salt for more economic product recovery. The salt to be converted is mixed with a substituting base compound with or without the presence of a dissolving solvent. The substituted base compound and/or the dissolving solvent are then removed from the solution by usual separation processes, such as evaporation or distillation, using conventional heating or electromagnetic waves. The substituted salt is precipitated by cooling from the solution with or without the presence of a base-extraction solvent or prepared by direct-extraction from the salt. A dissolving solvent, such as water, may be used to dissolve the unconverted salt that is then recycled or converted in a series of steps. Salt base-substitution also includes changing salt crystalline, such as shape or size, in the presence of another base compound. The amount of substituting base compound used may vary from 0.1–100, preferably 1–10, mole per mole of the carboxylic functional group.

In addition of washing with a non-salt-converting base-extraction solvent, the filter cake can be washed with a salt-converting base-extraction solvent or an acid-substitution solvent. This can be considered as a combined step of washing and the acid-substitution of the next step, and it is Lee's approach. However, washing has only little control on salt conversion and product properties. The instant invention prefers to either precipitate purified product during crystallization before filtering or separate the precipitate as a salt to be converted in the next step because both have better control on salt conversion, the extraction of base compound and impurities from the recovered product, and product particle size. For some basic salts, product particle size may be affected by salt particle size that can be controlled by spray drying, adjusting composition, residence time, temperature, agitation, or others.

Thus, processes for removing impurities comprises solution pretreatment, crystallization by cooling, crystallization by controlling composition with cooling, crystallizing salt in the presence of a base-extraction solvent, precipitating product in the presence of a base-extraction solvent, crystallization with direct-extraction from salt, crystallization with resalting, salt base-substitution, washing with a base-extraction solvent, leaching with a base-extraction solvent, or all possible combinations of these processes. In addition to removing impurities from the crude acid, excessive base compound is also removed from the washed cake to reduce the content of base compound in the finished product prepared by the following step.

Removing Residual Base Compound while Making Purified Product

This step recovers product from the salt in the washed cake if the amount of salt is significant, and/or removes residual base compound before making finished product. Processes for recovering product from purified salt comprises acid substitution; thermal decomposition; or electrolysis. Preferably, the product is recovered in the presence of base-extraction solvent. Because solution composition and temperature, agitation, and residence time may affect the particle shape and size of product, and they are preferably optimized with the extraction of base compound and impurities.

Acid Substitution

To convert the salt to product, an acid-substitution solvent is added to substitute and precipitate the product acid. The salt may be mixed with a base-extraction solvent. It is preferred to completely dissolve ether basic salts and common salts before adding an acid-substitution solvent, and the preferred solvent is water, methanol, ethanol, alkylene glycol, or a mixture of these. Carbonyl basic salts are insoluble in most solvents, and water is a preferred acid-substitution solvent. Water is preferably added in the presence of the base-extraction solvent, such as methanol, ethanol, acetone, tetrahydrofuran, or tetrahydropyran. Acid substituttion may be conducted under electromagnetic waves. Acid substitution with a base-extraction solvent reduces the inclusion of base compound and impurities in the recovered product.

An acid-substitution solvent may be an aliphatic carboxylic acid, an inorganic acid, water, or others. An aliphatic carboxylic acid may be formic acid, acetic acid, propionic acid, butyric acid, glycolic acid, lactic acid, malic acid, tartaric acid, mesotartaric acid, citric acid, monochloroacetic acid, monobromoacetic acid, mononitroacetic acid, trifluoroacetic acid, and trichloroacetic acid; and an inorganic acid may be nitric acid, hydrochloric acid, hydrogen bromide, hydrogen iodide, sulfuric acid, phosphoric acid, and perchloric acid. As discussed before, water or a base-extraction solvent can be an acid-substitution solvent for carbonyl basic salts. An acid-substitution solvent can be a mixture of these acids in any proportion, or a mixture of these acids with a dissolving solvent or a base-extraction solvent in a proportion that the acid is greater than 1% by weight.

For ether basic salts or common salts, the preferred acid-substitution solvent is aliphatic carboxylic acid, and the most preferable is acetic acid. For carbonyl basic salts, water is preferred. The amount of acid-substitution solvent added is 0.5–100 mole per mole of carboxylic functional group in the aromatic polycarboxylic acid. It is usually added in an amount of slightly more than the mole parts of the carboxylic functional group.

Thermal Decomposition

Heat is added to the purified salt to thermally decompose the base compound in a range of temperature between 50–350° C. The salt may be mixed with a base-extraction solvent having desired boiling temperature that can also be adjusted by pressure. The preferred base-extraction compound is water, steam, or an alcohol. The heat may be added by heat transferring, such as thermal conduction, or direct contacting with a heating medium.

In addition to the conventional process of heating, the salt may be thermally decomposed under electromagnetic waves. Preferably, the salt is mixed with a base-extraction solvent, such as water, steam, or an alcohol, in any proportion that may dissolve or acid-substitute the salt and absorb the wave to assist the decomposition. The wave thermally agitates the molecules and separates them from the product crystalline that is transparent to the wave, and decomposes the solution to a mixture of recovered product and unconverted salt. Maintaining a proper solvent concentration and temperature allows the solution to be decomposed continuously by the wave. The base-extraction solvent may also be added in a series of steps to the mixture for further decomposition. The unconverted salt may be separated from the recovered product by dissolving in a solvent, and the filtrate is recycled or thermally decomposed by the wave in a series of steps. Thus, this process may be used for batch or continuous processing. Thermal decomposition by electromagnetic waves requires significantly less energy and residence time compared with the conventional process. For instance, the residence time is estimated to be about 0.04–0.6 hours compared to about 2–12 hours of conventional processes. In addition, adding heat from inside out reduces the chance of including base compound in the recovered crystalline.

The decomposed base compound is preferred to be separated from the recovered product by usual processes, such as evaporation, suction under vacuum, distillation, absorbent, carrying by inert gas, steam, or a dissolving solvent, etc.

For carbonyl basic salts, thermal decomposition by direct contacting the salt with steam or by electromagnetic waves using water or steam as base-extraction solvent is preferred because it thermally decomposes and acid-substitutes the salt simultaneously. Its product particle size is then determined by salt particle size that is easier to control. Furthermore, this eliminates a step of filtration and the step of drying and pneumatically carrying by thermally decomposing and evaporating the residual salt and solvents in an alkylene glycol to be discussed below.

Electrolysis

Electric current is applied to a solution formed by dissolving the purified salt in a base-extraction solvent so that the cathode is concentrated with basic cations whereas the anode is concentrated with acidic anions. The product acid is precipitated around the anode if the applied electric current is sufficiently large enough. The alternative is to add acid-substitution solvent or heat around the favorable electrode to precipitate the product acid while keeping the basic cations apart under a moderate electric field to reduce the inclusion of base compound. The electrodes are separated by usual processes to minimize the disturbance of ions around the other electrode. The electrolysis is similar to the well-known electrolytic production of metal elements, and the invention is not limited to any specific electrolysis process. The magnitude of electric current used is not particular limited, it depends on the desired production rate or electric field to separate the ions. The electrode may use a material that is not reactive with the ions and not dissolved itself into solution to contaminate the product, or a material that can deposit the basic cation on the electrode for separation. The preferred base-extraction solvent is methanol, ethanol, alkylene glycol, or a mixture of these.

The recovered product crystalline may be separated by usual processes, and the filter cake is washed by a base-extraction solvent, an acid-substitution solvent, or a mixture of the solvents in any proportion. Some recovered products may be directly treated without separation by the following step.

Prior art uses only washing to remove residual base compound or convert salt to product, and it is insufficient to remove the base compound to a satisfactory level. The finished product has high content of residual base compound because the washed cake contains significant excessive base compound, the product is recovered without extracting residual base compound from crystalline, the purified solution containing excessive base compound is directly used for thermal decomposition, the base compound is refluxed to the thermally decomposed solution, or using washing for salt conversion by leaving unconverted salt in product, etc.

On the other hand, the invention tries to reduce the residual base compound by removing excessive base compound from the salt and extracting the residual compound from the recovered product. However, it is inevitable for the recovered product to contact base compound because it is a constituent of salt. Thus, these efforts can reduce but cannot totally remove the residual base compound from the recovered product. Some of the previous steps for removing base compound may be eliminated by having higher residual base compound in the recovered product. Since removing the residual base compound is a difficult process. Therefore, it is preferred to minimize the residual base compound in the recovered product.

The invention provides the following new processes for removing the residual base compound from the recovered product to make a finished product suitable for making polyesters. The new processes includes leaching; stripping; thermal agitating with electromagnetic waves; evaporation with thermal decomposition; or a combination of these processes.

The recovered product may be leached by mixing with a base-extraction solvent at a predetermined amount and temperature and re-filtered for one or more times. Processes for leaching or stripping traced solvent from filter cake are already well known, and the invention is not limited to any specific one. Leaching or stripping removes only the absorbed or entrapped but not the included base compound.

Thermal agitating with electromagnetic waves applies the wave to the recovered product or a mixture of the product with a base-extraction solvent. The process is similar to thermal decomposition by electromagnetic waves with emphasis on removing the residual salt included inside the recovered product. The wave is selectively absorbed by the residual base compound and solvents that induces thermal agitation to heat and drive the ions, whether adsorbed on surfaces or included inside crystals, out of the crystalline transparent to the wave. The decomposed base compound and other solvents are then separated as vapor; as liquid by an absorbent; or leached away by a base-extraction solvent surrounding the crystalline. The base extraction solvent may be added continuously or seriously to the cake for a predetermined duration or number of time to assist the decomposition of traced salt. This process removes the residual base compound and dries the product crystalline simultaneously.

Evaporation with thermal decomposition evaporates residual solvents, such as water or acetic acid, and thermally decomposes the residual base compound between 50–350° C., and preferably 90–210° C. The recovered product is mixed with 1) a monomer to be reacted with the product acid to make a polyester, such as an oligomer with a size of chain varying from 1–100 basic units, or 2) a base-extraction solvent, such as water at an elevated temperature. Preferably, it is mixed with the monomer, and alkylene glycol is the most typical monomer that will be used for illustration in the instant invention. The high boiling temperature of alkylene glycol is used to thermally decompose the residual salt and evaporate the residual solvent out of the solution. In addition, alkylene glycol is a structural unit of polyester, the solution or the filter cake can be directly used for producing the polyester. This makes the drying and pneumatically carrying steps unnecessary. If a polyester plant is not integrated with the purification plant, then this process can be conducted at either site. It is preferred to use heat transferring or thermal agitating under electromagnetic waves to avoid introducing another component. The evaporated residual solvent is removed by suction or other proper process. The preferred amount of alkylene glycol is the amount required for polymerization so that the treated solution can be directly used for making polyesters. This step can also be used in the predominant process to eliminate the drying and pneumatically carrying steps by mixing the pre-dried finished product with an alkylene glycol. The treated solution is different from the decomposed solution in product recovery that contains significant amount of base compound and other solvents and is unsuitable for making polyesters.

The base-extraction solvent used in product recovering, washing, leaching, stripping, thermal agitating with electromagnetic waves, or evaporation with thermal decomposition may or may not be the same. The amount of base-extraction solvent used is not particular limited, preferable in 0.5–1000 mole per mole of the carboxylic functional group.

If evaporation with thermal decomposition by alkylene glycol is not used to remove residual base compound, or if it is necessary, the purified product is dried to remove the residual solvents by blowing inert gas as in the predominant process. The alternative is to dry by using electromagnetic waves as described previously.

The purification method by solvent extraction may be conducted under an atmosphere of air, steam, inert gas, such as nitrogen, argon, or helium, or reductive gas, such as hydrogen or lower hydrocarbon gas. The method can be used for batch, semi-batch, or continuos processing.

Recycling improves the efficiency of product recovery and solvent usage. For instance, filtrates may be recycled or used for washing or leaching to a previous step to reduce the solvent requirement and improve product recovery. The recycling filtrates may be treated or untreated. The filtrate may be treated by any suitable process, such as distillation, filtration, centrifugation, sedimentation, evaporation, cooling, adding more solvent, or any combination of these processes. Processes for recycling to improve efficiency are already well known, the method will not be limited to any specific one.

The impurities from the disclosed method are, unexpectedly and surprisingly, undetectable by current standard HPLC method. Compared with the product purity from the prior art, the difference is about two orders of magnitude. The color from intentionally burnt sample meets the current standard, it implies that the base compound has been removed to a satisfactory level. PTA in lower impurity provides many potential advantages: larger molecular weight in polymerization, stronger and finer fiber, less oxygen penetration through bottles, faster spinning speed for producing fibers, and many more advantages yet to be discovered.

Description of a Preferred Process for Producing High Purity Aromatic Polycarboxylic Acids A new combination of the purification method discussed above with the prior art of oxidation and the recovery of solvents and catalysts provides a process with substantially less capital and production costs. The process can be applied for all aromatic polycarboxylic acids produced through the oxidation of the corresponding alkyl group with molecular oxygen. Examples of such acids are PTA, IPA, TMA, 2,6-NDA, 2,7-NDA, and others. Since PTA is the most typical process and it will be used for illustrations.

The combination reduces two sets of process steps into one set to produce aromatic polycarboxylic acid in high purity. This is accomplished by taking advantages of the following special features and advantages found in the disclosed purification method.

1) In addition to CTA, the purification method may directly take the reactor effluent as feed without separating CTA. The effluent contains other material, such as catalysts (including catalyst promoters) and acetic acid, that can be separated from the product in the purification process. This allows reducing two sets of process steps in the predominant process to one set to significantly reduce the capital and production costs.

2) The prior art has to consider factors such as viscosity, particle size, product recovery, and inclusion of impurity that can be circumvented by the proposed crystallization with direct-extraction from salt. In addition, the base-extraction solvent can be used to adjust the viscosity of slurry for separation and transportation.

3) The purification method can remove more impurities than the hydrogenation unit in the predominant process. This allows the oxidation reactor to operate at more economical condition, such as a severity for lower hydrocarbon combustion and catalyst consumption, etc.

4) The purification method does not require crystallizer for crystallization.

5) The purification method may eliminate drying and pneumatically carrying steps by using evaporation with thermal decomposition by alkylene glycol.

6) The purification method uses physical separation rather than chemical reaction to remove impurities, this requires less capital and production costs for purification.

7) The purification method produces product purity significantly higher than the predominant process. This provides many potential advantages as described previously.

The invention takes these synergistic advantages and unobvious features to provide an unsuggested combination that requires substantially less capital and production costs. The combination comprises oxidizing; dissolving crude acid; removing impurities and base compound from the purified salt; removing residual base compound while recovering purified product from the salt; and recovering solvents and catalysts. The process steps are described as follows:

Oxidizing

This step produces aromatic polycarboxylic acids through the oxidation of the corresponding alkyl group with molecular oxygen. The oxidation of aromatic polycarboxylic acid has been extensively studied in the last 50 years, the invention may use any previously known prior art and is not limited to any specific one.

A process developed by Mid-Century is a widely adopted oxidizing process which uses acetic acid as a solvent to assist slurry mixing and circulation; heavy metals, e.g., cobalt and manganese, as catalysts; and a bromine-containing compound as promoter. Reaction conditions are generally in the range of 175–230° C. and 1500–3000 kPa.

The feed may include recycles containing catalysts, reactor solvent, or intermediate products from the steps of dissolving a salt formed by crude acid with a base compound in a dissolving solvent; removing impurities and base compound from the purified salt; and recovering solvents and catalysts.

Dissolving Crude Acid

Dissolving the crude aromatic polycarboxylic acid in a base compound has already been described. As discussed previously, the purification method can take reactor effluent or CTA from the predominant process as a crude acid. Therefore, there are many alternatives between the two extremes to prepare the crude acid. For instance, if the slurry from flashed reactor effluent is used as a crude acid, then the reactor solvent and catalysts will be presented in filtrates with impurities that can be subsequently recovered in the step of recovering solvents and catalysts. The alternative is to separate reactor solvent and catalysts from the crude acid by processes taught in previously known prior art, such as flashing, evaporation, heating/cooling, crystallization, filtration, centrifugal classifier, distillation, classification column, fluid hydrocyclone, a cyclone separator, settling, replacement of mother liquor with water, membrane, or from any intermediate step of preparing CTA in the predominated process. The separated mother liquor is either recycled to reactor or sent to the step of recovering solvents and catalysts. The instant invention is not limited to any specific process for separating the reactor effluent. However, one of preferable separating processes is to evaporate most of mother liquor out of the flashed reactor effluent, and recycle a small portion of mother liquor containing catalysts separated from the crude acid. The evaporation may or may not de conducted under electromagnetic waves. This approach recovers most of crude acid from reactor effluent without using crystallization.

The other source of crude acids may be from recycled filtrates, treated or untreated, or from the step of recovering solvents and catalysts.

Removing Impurities and Excessive Base Compound

Removing impurities has been described previously. As discussed before, crystallization by controlling composition with cooling can reduce the number of crystallizer, crystallization with direct-extraction from salt eliminates the crystallizer for crystallization.

The filtrate can be recycled to the other step, treated or untreated, or sent to the step of recovering solvents and catalysts. Some impurities have to be removed from this step to avoid accumulation, and this can be accomplished by any proper process. One of the examples is to evaporate solvents from a selected filtrate containing significant amount of impurities, and the bottom is then directly recycled or treated with a product recovering step to convert the salt to impurities before recycling.

Removing Residual Base Compound while Making Purified Product

This step has been described previously. If evaporation with thermal decomposition by alkylene glycol is used to remove residual base compound, then the drying and pneumatically carrying steps in the state of art process will be unnecessary.

The particle sizes obtained from acid substitution are generally finer, but more uniform, than those obtained from the existing PTA processes. If alkylene glycol is used for removing the traced basic compound, then the mixture can be used directly for making PET. However, if it is necessary, re-dissolving and re-crystallization can adjust the bulk density of PTA. This can be achieved by a number of processes used in existing manufacturing plants. The re-crystallized PTA are not only similar to current commercial PTA in bulk density but also further purified to contain fewer impurities.

Recovering Solvents and Catalysts

In addition to using previously known prior art for recovering reactor solvent, water, catalysts, this step also recovers base compound; base-extraction solvent; acid-substitution solvent if it is used for recovering product and is different from reactor solvent; and dissolving solvent if it is used and different from water. Besides, residual impurities and product may possibly present from direct recycling of filtrates from purification steps.

Not all components have to be recovered to their pure forms. Some may be recovered as a mixture. For instance, in the dissolving crude acid step, the base compound and dissolving solvent can be used as a mixture. Furthermore, if the mixture contains some acid-substitution solvents, it does not have significant impact on the efficiency of purification.

Among the solvents, some may form azeotropic mixture. If acid substitution is used for recovering product then the base compound and the acid solvent may form electrolytes. However, processes for separating these components are already well known, such as distillation, filtration, centrifugation, sedimentation, evaporation, thermal decomposition, cooling, membrane, stronger base substitution, stronger acid substitution, adding other component to break an azeotropic mixture, and others. The invention may also use electromagnetic waves for evaporation, distillation, and thermal decomposition, and others.

Conclusion

Thus, the purification method of the instant invention removes not only impurities from crude aromatic polycarboxylic acids, it also provides procedures to remove the base compound used for purification that will otherwise contaminate the finished product. The invention solves an unsolved or unknown problem, and it makes purification by solvent extraction practical.

The purification method reduces the number of crystallizers for crystallization or totally eliminate them. Using alkylene glycol to remove residual base compound eliminates the drying and pneumatically carrying steps required in the prior art.

Compared to the purity of the prior art, the improvement of product purity is about two orders of magnitude with undetectable impurity by standard HPLC measurement. This provides many potential advantages such as making new fibers that are stronger and finer, increasing PET fiber production rate with higher spinning speed, applying PET bottles for new uses by reducing oxygen penetration rate, and many more advantages yet to be discovered.

By taking advantages of some special features and advantages found in the purification method, the combination of the purification method with the prior art in oxidation and the recovery of solvents and catalysts reduces two sets of process steps in the predominant process into one set. This unsuggested combination substantially reduces capital and production costs to produce high purity aromatic polycarboxylic acids.

In addition to aromatic polycarboxylic acids, the purification method can be used for the purification of organic acids containing impurities having close physical and chemical properties. The impurities may have different number of acid functional group; an acid group substituted by other functional group; the acid functional group at different positions; or the same acid group at the same position but with hydrogen substituted by other functional group, etc.

Accordingly, the scope of the invention should be determined not by the embodiments illustrated, but by the appended claims and their legal equivalents. The invention is further illustrated by the following examples.

REFERENCE EXAMPLE

A sample of crude terephthalic acid (CTA) from a PTA manufacturer with the levels of impurities shown in Table 1 was used in the experiments:

TABLE 1

|  | 4-CBA | Benzoic Acid | p-Toluic Acid |
|---|---|---|---|
| PTA(ppmw) | 2436 | 1097 | 515 |

Where ppmw means parts per million by weight.

Comparative Example 1

A CTA with similar composition from Table 1 is subject to a conventional hydrogenation purification method as discussed in the prior art to give a PTA product with the impurity level shown in Table 2:

TABLE 2

|  | 4-CBA | Benzoic Acid | p-Toluic Acid |
|---|---|---|---|
| PTA(ppmw) | 15 | Undetectable | 141 |

Similarly, the PTA product from another source contained the levels of impurities shown in Table 3:

TABLE 3

|  | 4-CBA | Benzoic Acid | p-Toluic Acid |
|---|---|---|---|
| PTA(ppmw) | 25 | 52 | 150 |

The impurity levels in the purified products represent typical commercially available polymer-grade terephthalic acid.

Comparative Example 2 (Removing Impurities but not Base Compound)

A sample of 150 grams of CTA as described in Table 1 was mixed with 198 grams of morpholine and 180 grams of water. The solution was raised to 100° C. to completely dissolve the CTA and then cooled to room temperature for precipitation. The slurry was filtered to separate from the mother liquor, and the filter cake was subsequently washed with morpholine to obtain 196 grams of wet cake. The recovered solids were then mixed with 84 grams of water and 22 grams of morpholine. The solution temperature was then raised to 110° C. to evaporate 57 c.c. of condensate, and the solution was then cooled to room temperature for precipitation. The filter cake was subsequently washed with morpholine to obtain 145 grams of purified salt. The salt was then mixed with 235 grams of acetic acid and 14 grams of water to precipitate PTA. The filter cake was washed by about 600 grams of water. The wet cake was then dried in an oven at about 275° C. for 4 hours to obtain 40 grams of dried purified terephthalic acid. Analysis with HPLC showed the impurities in Table 4. However, the measured B-Value representing the color of cake was 6.5, four times higher than the standard value of 1.6. This indicated the PTA contained significant amount of morpholine.

TABLE 4

|  | 4-CBA | Benzoic Acid | p-Toluic Acid |
|---|---|---|---|
| PTA(ppmw) | Undetectable | Undetectable | Undetectable |

Comparative Example 3 (Precipitating Product by Directly Adding Acetic Acid)

A sample of 3 grams of CTA as described in Table 1 was totally dissolved at room temperature into a solution containing 5.010 grams of triethylamine and 9.047 grams of methanol. 7.570 grams of acetic acid were then added to precipitate crystals, which were then filtered and dried to 2.179 grams of terephthalic acid. Analysis with HPLC showed the acid contained the impurities as shown in the Table 5.

TABLE 5

|  | 4-CBA | Benzoic Acid | p-Toluic Acid |
|---|---|---|---|
| PTA(ppmw) | 2471 | 844 | 471 |

Example 1 (Crystallization by Direct-extraction from Precipitate with Leaching)

A sample of 40 grams of CTA as described in Table 1 was mixed with 52 grams of morpholine and 48 grams of water. The solution was heated to 110° C. to dissolve the CTA and evaporate 29 c.c. of condensate, and then cooled to room temperature for precipitation. The filter cake was subsequently washed and leached by methanol to obtain 55 grams of wet cake. The wet cake was then mixed with 30 grams of methanol, and then 85 grams of acetic acid was added to the solution for precipitating terephthalic acid. The wet cake was washed with 35 grams of methanol, and leached with 35 grams of methanol for three times to obtain 31.5 grams of wet cake. The wet cake was then dried in an oven at about 250° C. for 4 hours to obtain 24 grams of dried cake. The B-Value of the cake was 2.73 that was still higher the standard, and the analysis with HPLC showed the PTA containing the impurities in Table 6.

TABLE 6

|  | 4-CBA | Benzoic Acid | p-Toluic Acid |
|---|---|---|---|
| PTA(ppmw) | 20.8 | Undetectable | Undetectable |

Example 2 (Crystallization with Resalting with Evaporating and Thermal Decomposing)

A sample of 925 grams of CTA as described in Table 1 was dissolved in 1103 grams of morpholine and 1205 grams of water. The solution was heated to 110° C. and evaporated to about 404 c.c. of condensate and stopped before the sudden crystallization. The solution was cooled to room temperature for 4 hours to precipitate crystalline. 250 grams of ethanol was added to dilute the slurry, and the filter cake was then washed and leached by about 750 grams of ethanol to obtain 1455 grams of salt. 1005 grams of the salt was dissolved in 465 grams of water. The solution was heated to 109° C. and suddenly crystallized after evaporating about 280 c.c. of condensate. The salt was leached by 650 grams of ethanol, and the slurry was filtered and washed by 250 grams of ethanol to obtain 702 grams of purified salt. 35 grams of the salt was dissolved in 40 grams of water and 40 grams of ethanol, and 60 grams of acetic acid was then added to the solution to precipitate the product crystalline. The filter cake was washed and leached by about 200 grams of water for 3 times to obtain 27.5 grams of wet cake that was then mixed with 130 grams of EG. The solution was heated to about 150–165° C. under normal pressure until no more brown liquid was condensed and separated from the solution. The hot solution was then immediately filtered, washed and leached by about 300 grams of water to obtain 15.4 grams of wet cake. The cake was then dried in a microwave oven for 20 minutes set at median power level with an absorbent underneath the cake, the cake was then dried in an oven at about 250° C. for 4 hours to obtain 11.6 grams of dried cake. The B-Value of the cake was 1.58 that met the standard, and the analysis with HPLC showed the PTA containing the impurities in Table 7.

TABLE 7

|  | 4-CBA | Benzoic Acid | p-Toluic Acid |
|---|---|---|---|
| PTA(ppmw) | Undetectable | Undetectable | Undetectable |

Example 3 (Simulating Reactor Effluent Condition with Leaching)

A sample of 150 grams of CTA as described in Table 1 was dissolved at room temperature into a solution with composition close to flashed reactor effluent compositions. The solution contained 202 grams of morpholine, 191 grams of water, 29 grams of 48% hydrobromic acid, 0.23 grams of cobalt acetate tetrahydrate, 0.3 grams of magnesium acetic tetrahydrate, and 60 grams of acetic acid. The temperature of this solution was raised to 110° C. to dissolve the CTA and evaporate 79 c.c. of condensate. The solution was then cooled to room temperature for precipitation, and the filter cake was subsequently washed and leached by methanol to obtain 278 grams of wet cake. The wet cake was then mixed with 133 grams of water, and the solution temperature was then raised to 110° C. to evaporate 88 c.c. of condensate, and the solution was then cooled to room temperature for precipitation. The filter cake was washed and leached by methanol to obtain 160 grams of wet cake. The wet cake was then mixed with 160 grams of methanol, and 180 grams of acetic acid was then added to the solution for precipitating terephthalic acid. The wet cake was washed and leached with 500 grams of water, and leached with 35 grams of methanol for 3 times to obtain 123 grams of wet cake. The wet cake was dried in a microwave oven for 20 minutes set at median power level with an absorbent underneath the cake, the cake was then dried in an oven at about 250° C. for 4 hours to obtain 73 grams of dried cake. The B-Value of the cake was 2.22, all metal contents are less than standard specification, and analysis with HPLC showed the PTA containing the impurities shown in Table 8

TABLE 8

|  | 4-CBA | Benzoic Acid | p-Toluic Acid |
|---|---|---|---|
| PTA(ppmw) | Undetectable | Undetectable | Undetectable |

Example 4 (Thermal Decomposition by Electromagnetic Waves)

A sample of 10.05 grams of purified salt from Example 2 was dissolved in 6 grams of water. The solution was heated in a 600 watt-microwave oven for 3 minutes and the residual mixture contained about 9.29 grams of solids. The solids was then mixed in 6.27 grams of water and heated in the oven for 3 minutes to obtain 8.82 grams of solids. The solids was then mixed in 6.66 grams of water and heated for 3 minutes to obtain 8.49 grams of solids. The solids was then mixed in 10.85 grams of water and heated in the oven for 4 minutes to obtain 8.14 grams of solids. The solids was then mixed in 9.59 grams of water and heated in the oven for 3 minutes to obtain 7.82 grams of solids. In each step, the reduction of weight was from the salt decomposed.

Example 5 (Crude NDA)

A sample of 150 grams of crude 2-6 and 2-7 NDA was mixed with 161 grams of morpholine and 180 grams of water. The temperature of this solution was raised to 110° C. to evaporate solvents by 86 c.c. The solution was then cooled to precipitate crystals that were then filtered to separate from the mother liquor. The filter cake was subsequently washed with a 10 wt % water mixture in morpholine to obtain 186 grams of wet cake. The wet cake is then re-dissolved in 72 grams of water and 18 grams of morpholine, and the solution was then heated to vaporize 35 c.c. of condensate. After cooling the solution for precipitation, filtering, and washing with a mixture of solvent containing 10 wt % water in morpholine, 158 grams of wet cake was obtained. A mixture of 16 grams of water and 158 grams of acetic acid was then added to the purified salt to precipitate the product acid. It was then filtered, washed with water, dried to obtain 85 grams of purified acid. The crude NDA was purified to 99.993%. Analysis with Capillary Electro-phoresis of the crude acid showed 11 peaks with time and area at (8.86,3.824), (8.92,2.891), (8.92,5.518), (9.06,10.038), (9.18,36.226), (9.45,18.536), (9.52,13.944), (9.57,8.298), (11.87,0.106), (11.99,0.598). Electro-phoresis of the purified acid showed 2 peaks with time and area at (9.49,99.993) and (9.55,0.007).

Example 6 (Dissolving by Microwaves and Crystallization in Ethanol Using NMP)

A sample of 12.5 grams of CTA as described in Table 1 was mixed in 60 grams of NMP preheated in a 600 watt-microwave oven for 30 seconds. The CTA was completely dissolved in 3.5 minutes using low power level of the oven. 13 grams of ethanol was added to solution during crystallization by cooling the solution in an ice bath for about 60 minutes. The salt was then filtered and washed by the solvent mixed by 50% of ethanol and 50% NMP to obtain 26.2 grams of salt. The salt was mixed with 31 grams of NMP and redissolved in the microwave oven for 2.7 minutes using low power level. 15 grams of ethanol was added to solution during crystallization by cooling the solution in an ice bath for about 60 minutes. The salt was then filtered and washed by the solvent mixed by 50% of ethanol and 50% NMP to obtain 16 grams of purified salt. 3 grams of the purified salt was put between a stack of filter paper socked with water. The microwave oven was set at low power level to thermally decompose the purified until no change of the weight to obtain 1.2 grams of PTA. Table 9 shows the impurity analyzed with HPLC.

TABLE 9

|  | 4-CBA | Benzoic Acid | p-Toluic Acid |
|---|---|---|---|
| PTA(ppmw) | Undetectable | Undetectable | Undetectable |

The preceding examples were presented to facilitate an understanding of the process of the present invention, and are not intended to limit the scope of the present invention to specific compounds or process steps. The scope of the invention is defined by the claims that follow.

What is claimed is:

1. A method for making a purified organic acid, oligomer, or derivative thereof, comprising:
    dissolving a crude organic acid, or derivative thereof, in a base compound;
    removing impurities;
    recovering the purified organic acid or the derivative thereof; and
    removing base compound absorbed, entrapped, and included in the purified organic acid or the derivative thereof.

2. The method as claimed in claim 1, wherein said crude organic, or said derivative thereof, is dissolved by thermal agitating under electromagnetic waves.

3. The method as claimed in claim 1, wherein said crude organic acid, or said derivative thereof, is selected from the group of terephthalic acid, isophthalic acid, orthophthalic acid, trimellitic acid, hemimellitic acid, trimesic acid, pyromellitic acid, mellific acid, naphthalene dicarboxylic acid, naphthalene dicarboxylic acid, naphthalene tricarboxylic acid, naphthalene tetracarboxylic acid, anthracene dicarboxylic acid, anthracene tricarboxylic acid, anthracene tetracarboxylic acid, naphthalene dicarboxylic acid, methyl ester dimethyl terephthalate, dimethyl-naphthalene dicarboxylate, hydrolyzed polyester, and combinations thereof.

4. The method as claimed in claim 1, wherein said crude organic acid, or said derivative thereof, is dissolved in the base compound and a dissolving solvent.

5. The method as claimed in claim 1, wherein the base compound absorbed, entrapped, and included in the purified organic acid, or the derivative thereof, is removed by thermal agitating with electromagnetic waves or evaporation with thermal decomposition.

6. A method for making a purified organic acid, oligomer, or derivative thereof, comprising:
    dissolving a salt formed by a crude organic acid, or a derivative thereof, and a base compound;
    removing impurities and excessive base compound from the salt of the crude organic acid or the derivative thereof using one or more processes selected from a group consisting of pretreatment, crystallization by cooling, crystallization by controlling composition with cooling, crystallizing salt in the presence of a base extraction solvent, precipitating product in the presence of a base-extraction solvent, crystallization with direct-extraction from salt, crystallization with resalting, salt base-substitution, washing with a baseextraction solvent, and leaching with a base-extraction solvent;
    recovering the purified organic acid or the derivative thereof from the salt; and
    removing base compound absorbed, entrapped, and included in the purified organic acid or the derivative thereof.

7. The method as claimed in claim 6, wherein said crude organic acid, or said derivative thereof, is selected from the group of terephthalic acid, isophthalic acid, orthophthalic acid, trimellitic acid, hemimellitic acid, trimesic acid, pyromelltic acid, mellitic acid, naphthalene dicarboxylic acid, naphthalene dicarboxylic acid, naphthalene tricarboxylic acid, naphthalene tetracarboxylic acid, anthracene dicarboxylic acid, anthracene tricarboxylic acid, anthracene tetracarboxylic acid, naphthalene dicarboxylic acid, methyl ester dimethyl terephthalate, dimethyl-naphthalene dicarboxylate, hydrolyzed polyester, and combinations thereof.

8. The method as claimed in claim 6, wherein said crude organic acid is a terephthalic acid or an isophthalic acid.

9. The method as claimed in claim 6, wherein said crude organic acid is a 2,6-naphthalene dicarboxylic acid, a 2,7-naphthalene dicarboxylic acid, or a mixture of naphthalene dicarboxylic acids.

10. The method as claimed in claim 6, wherein said salt is dissolved by thermal agitating under electromagnetic waves.

11. The method as claimed in claim 6, wherein said base compound is an amide compound.

12. The method as claimed in claim 6, wherein said salt is dissolved in the base compound and a dissolving solvent.

13. The method as claimed in claim 6, wherein said base compound is an oxygen-containing base compound.

14. The method as claimed in claim 6, wherein said base compound is N-methyl-pyrrolidone.

15. The method as claimed in claim 6, wherein said crude aromatic polycarboxylic acid is a hydrolyzed polyester resin.

16. The method as claimed in claim 6, wherein said base-extraction solvent comprises water, methanol, ethanol, alkylene glycol, acetone, tetrahydrofuran, or tetrahydropyran.

17. The method as claimed in claim 6, wherein recovering the purified organic acid, or the derivative from the salt is by adding an acid-substitution solvent in the presence of a base-extraction solvent.

18. The method as claimed in claim 6, wherein recovering the purified organic acid, or the derivative from the salt is by thermal decomposition using electromagnetic waves.

19. The method as claimed in claim 6, wherein the base compound absorbed, entrapped, and included in the purified organic acid, or the derivative thereof, is removed by thermal agitating with electromagnetic waves or evaporation with thermal decomposition.

20. A method for making a purified organic acid, oligomer, or derivative thereof, comprising:

dissolving a salt formed by a crude organic acid, or a derivative thereof, and a base compound; and removing impurities from the salt using one or more processes selected from a group consisting of crystallization with direct-extraction from salt, crystallization with resalting using a base-extraction solvent, and salt base-substitution.

21. The method as claimed in claim 20, wherein said crude organic acid is a crude aromatic polycarboxylic acid.

22. The method as claimed in claim 20, wherein said salt is dissolved by thermal agitating under electromagnetic waves.

23. The method as claimed in claim 20, wherein said salt is dissolved in a dissolving solvent.

24. The method as claimed in claim 20, wherein said base compound is morpholine and the salt is dissolved in water.

25. The method as claimed in claim 20, wherein said base compound is an amide compound.

26. The method as claimed in claim 20, wherein said base compound is an amine compound, and the salt is dissolved in water or an alcohol.

27. The method as claimed in claim 20, further including recovering the purified organic acid, oligomer, or derivative thereof from the salt by acid-substitution, thermal decomposition, or electrolysis.

28. The method as claimed in claim 27, further comprising removing residual base compound in the recovered purified organic acid, oligomer, or derivative thereof.

29. A method for producing a purified aromatic polycarboxylic acid, oligomer, or derivative thereof, comprising the steps of:

preparing a crude aromatic polycarboxylic acid, or derivative, by oxidizing alkyl groups on an aromatic compound with molecular oxygen in the presence of catalysts and solvents;

separating said solvents from the crude aromatic polycarboxylic acid, or derivative, by flashing and evaporation;

dissolving a salt formed by the crude aromatic polycarboxylic acid, or derivative and a base compound;

removing impurities from the salt of the crude aromatic polycarboxylic acid, or derivative;

recovering said purified aromatic polycarboxylic acid, or derivative from the salt; and removing residual base compound in the purified aromatic carboxylic acid, oligomer, or derivative.

30. The method as claimed in claim 29, wherein said salt is dissolved in said base compound and a dissolving solvent.

31. The method as claimed in claim 29, wherein the catalysts are separated by filtering or washing the crude aromatic polycarboxylic acid, or derivative.

32. The method as claimed in claim 29, wherein said base compound is morpholine and the salt is dissolved in water.

33. The method as claimed in claim 29, wherein said base compound is an oxygen-containing base compound.

34. The method as claimed in claim 29, wherein said base compound is an amine compound, and the salt is dissolved in water or an alcohol.

35. A method for making a purified organic acid, oligomer, or derivative thereof, comprising:

dissolving a crude organic acid, or a derivative thereof, containing impurities in a base compound by thermal agitating under electromagnetic waves; and removing the impurities.

36. The method as claimed in claim 35, wherein the crude organic acid, or the derivative thereof, is dissolved in the base compound and a dissolving solvent.

37. The method as claimed in claim 35, further comprising recovering the purified organic acid, oligomer, or derivative thereof.

38. The method as claimed in claim 35, wherein residual base compound in the purified organic acid, oligomer, or derivative thereof is removed after recovering the purified organic acid, oligomer, or derivative thereof.

* * * * *